United States Patent [19]

Ancel et al.

[11] Patent Number: 5,449,844

[45] Date of Patent: Sep. 12, 1995

[54] NEW INTERMEDIATES FOR PREPARING VITAMINS A AND E AND CAROTENOIDS

[75] Inventors: Jean-Erick Ancel, Rouen; Bienayme, Hugues, Lyon; Lucette Duhamel; Pierre Duhamel, both of Mont Saint Aignan, all of France

[73] Assignee: Rhone-Poulenc Nutrition Animale, Commentry, France

[21] Appl. No.: 982,675

[22] Filed: Nov. 27, 1992

[30] Foreign Application Priority Data

Nov. 28, 1991 [FR] France ............................... 91 14699

[51] Int. Cl.$^6$ ............................................ C07C 43/00
[52] U.S. Cl. ................................. 568/691; 568/378; 568/403; 568/404
[58] Field of Search ................ 568/378, 691, 403, 404

[56] References Cited

U.S. PATENT DOCUMENTS

| | | | |
|---|---|---|---|
| 2,482,725 | 12/1946 | Bramwyche et al. | 260/614 |
| 2,667,517 | 6/1951 | Longley | 260/614 |
| 4,331,814 | 5/1982 | Chabardés et al. | 560/255 |

OTHER PUBLICATIONS

G. Saucy and R. Marbet, Über eine neuartige Synthese von β-Ketoallenen durch Reaktion von Tertiaren Acetylencarbinolen mit Vinylathern Eine ergiebige Methode zur Darstellung des Pseudojonons und verwandter Verbingungen, 50:1158–1167 (1967).

Primary Examiner—Johann Richter
Assistant Examiner—K. Kestler
Attorney, Agent, or Firm—Finnegan, Henderson, Farabow, Garrett & Dunner

[57] ABSTRACT

The present invention relates to a new method of condensing polyenic compounds wherein a compound having the formula III

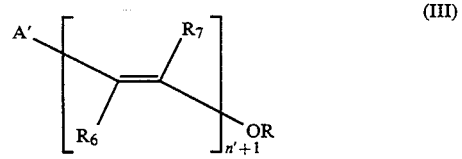

is condensed with a compound having the formula IV

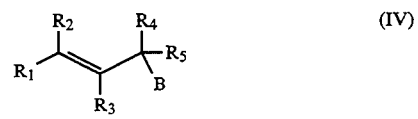

under the influence of a Lewis acid or a protic acid. $R_1$ through $R_7$ represent alkyl or alkenyl groups, A' is preferably chlorine, B is preferably a hydroxyl group, and n' is 0 to 10. The invention also relates to novel intermediates for use in the preparation of Vitamins A and E produced by means of the new method.

22 Claims, No Drawings

NEW INTERMEDIATES FOR PREPARING VITAMINS A AND E AND CAROTENOIDS

BACKGROUND OF THE INVENTION

The present invention relates to a new process for preparing vitamin A and its intermediates; it also relates to a new process for preparing intermediates of vitamin E and carotenoids.

Vitamins A and E have been prepared chemically for a long time. The preparation processes are numerous and varied. A relatively exhaustive account of the processes used industrially can be found in an article published by J. Paust in *Pure & Appl. Chem.*, Vol. 63(1):45–58, (1991).

In this article, Paust described various industrial techniques for carrying out the condensation of various polyenic units in order to arrive at vitamin A. This condensation is performed either via a sulphone (U.S. Pat. No. DE 2,202,689) or via an acetylenic compound which is used in a Grignard reaction (article which appeared in *Pure & Appl. Chem.* 47:183 (1976)) or finally via a Wittig reaction involving a phosphorus ylide (U.S. Pat. Nos. DE 1,046,046 and DE 1,026,475).

Each of these three techniques for condensing various polyenic units uses, as starting material, a relatively expensive intermediate which, on its own, will enable the condensation to be performed in each of the processes described, thus making this step particularly expensive in the case of all the processes described. Further, because the starting intermediates are expensive, a step for recycling or removing the by-products formed is essential in all these processes. Phosphonium is converted to phosphine oxide which has to be reduced to phosphine; the sulphonic derivative produces, at the end of the reaction a phenyl sulphinate which has to be recycled; during the reaction, the acetylenic derivative consumes magnesium which generates salts that have to be removed.

We therefore sought a new process for preparing vitamins A and E, which makes it possible to dispense with these sulphones, acetylenic compounds and phosphorous ylides.

SUMMARY OF INVENTION

Our invention relates to a new process for condensing polyenic compounds as required, e.g., in the preparation of Vitamin A and Vitamin E which does not use sulfonic compounds, phosphonium salts or acetylenic compounds. Specifically, it relates to a process for condensing polyenic compounds, which process comprises condensing a) a mono- or polyunsaturated compound having the formula III

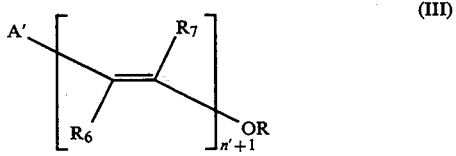

(III)

wherein
n' represents an integer from 0 to 10;
R represents an alkyl group, a silyl group having 1 to 3 carbon containing substituents selected from methyl, ethyl or phenyl groups, an alkylcarbonyl group or a tosyl group;
$R_6$ and $R_7$ each represent identical or different substituents chosen from hydrogen, alkyl and cyclic alkenyl radicals having 1 to 4 carbon atoms, and when n' is 1 or more, all $R_6$ and $R_7$ units need not be identical;
A represents hydrogen, a halogen chosen from chlorine and bromine, or an arylthio, arylseleno, acyloxy or trialkylsilyl group with b) a mono- or polyunsaturated allyl alcohol derivative having the formula IV

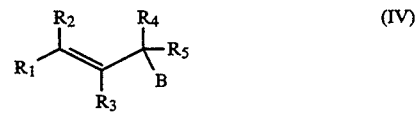

(IV)

wherein $R_1$, $R_2$, $R_3$, $R_4$ and $R_5$ represent hydrogen, an alkyl group having 1 to 20 carbon atoms or an alkenyl group having 2 to 20 carbon atoms or they may form, with one another, a cyclic, optionally substituted, terpenic, polyenic, alkylene or alkenylene chain, and B represents hydroxyl, an alkoxyl group having 1 to 6 carbon atoms, an alkyl carbonyl group, an aryloxy group, a silyloxy group or halogen.

The invention also relates to new intermediates for the preparation of Vitamin A which intermediates have the formula I

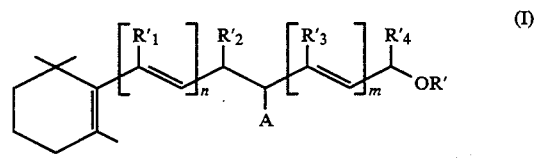

(I)

wherein:
n and m are integers equal to 0, 1, 2 or 3;
$R'_1$, $R'_2$, $R'_3$ and $R'_4$ represent the same or different radicals selected from hydrogen and alkyl groups having 1 to 6 carbon atoms and when n or m equals 2 or more, the groups represented by $R'_1$ or $R'_3$, as the case may be, can be the same or different within the unsaturated segment in which they appear;
A represents a halogen atom chosen from chlorine and bromine, an arylthio group or an arylseleno group, but not being bromine when n is 1 and m is 2; and
R' represents hydrogen, a bond with the carbon atom of the chain, an alkyl group, or an alkylcarbonyl group.

The compounds of formula I wherein A represents chlorine or bromine and wherein n+m equals 3 are preferred compounds of formula 1 as these lead directly to Vitamin A upon dehydrohalogenation,.

The invention further relates to new intermediates for the preparation of Vitamin E or carotenoids having the formula II:

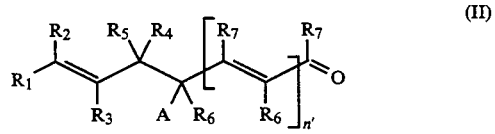

(II)

wherein
$R_1$, $R_2$, $R_3$, $R_4$, $R_5$, $R_6$ and $R_7$ each represent identical or different groups chosen from hydrogen, alkyl or cyclic alkenyl units, it being possible for two of the substituents to form a saturated or unsaturated ring with one another;

A represents a halogen chosen from chlorine and bromine, or an arylthio or arylseleno group; and n' is an integer from 0 to 10.

The intermediate of formulae I and II are prepared by the process of this invention.

DETAILED DESCRIPTION OF THE INVENTION

The process of this invention wherein a compound of formula III is condensed with a compound of formula IV is carried out in the presence of a Lewis acid or a protic acid, preferably in a solvent.

The Lewis acid or protic acid is chosen, in particular, from zinc chloride, boron trifluoride etherate, ferric chloride, trimethylsilyl triflate, stannous and stannic chlorides, formic acid, trichloroacetic acid, trifluoroacetic acid, trifluoromethanesulphonic acid, dimethyl tert-butylsilyl triflate, heterogeneous acid catalysts (Nafion resins), bismuth trichloride and titanium tetrachloride.

According to a preferred embodiment of the invention, the condensation can be performed in the presence of a solvent. The solvent is chosen from solvents such as in particular water, alcohols, nitriles, nitroalkanes, nitroaryls, halogenated aliphatic or aromatic solvents, sulphones or organic acids. The reaction can also be performed in a mixture of these solvents. The preferred solvents are water and alcohols.

The reaction temperature is preferably between −45° C. and 50° C., and still more preferably between −45° C. and room temperature.

The compounds of formula (IV) having the following formulae are preferably used for the preparation of intermediates for vitamin A:

compounds having 10 carbon atoms:

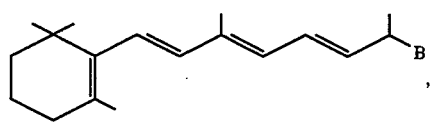

compounds having 13 carbon atoms:

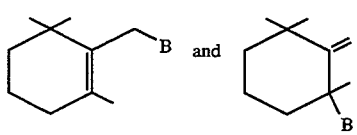

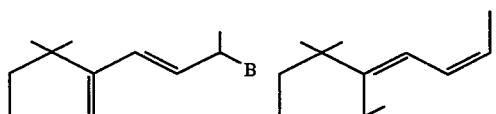

compounds having 15 carbon atoms:

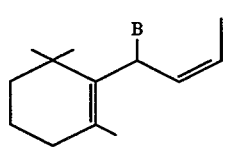

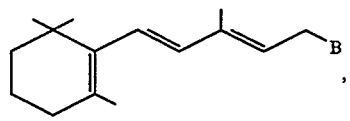

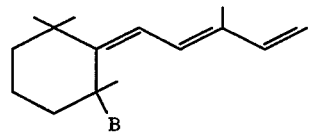

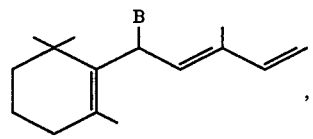

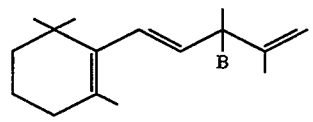

compounds having 18 carbon atoms:

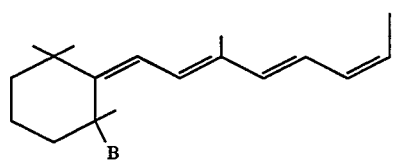

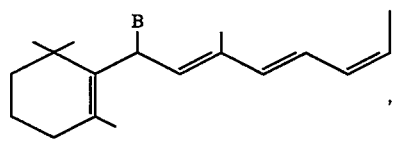

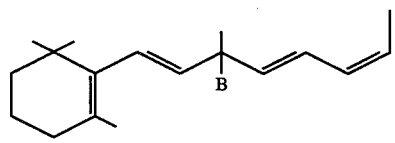

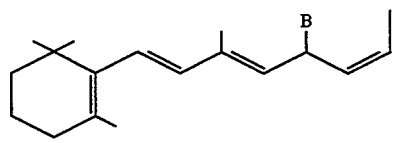

Still with respect to the synthesis of vitamin A, of the mono- or polyunsaturated compounds of formula (III), the use of the following compounds is preferred:
compounds having 10 carbon atoms:

compounds having 7 carbon atoms:

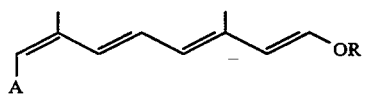

compounds having 5 carbon atoms:

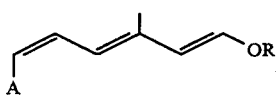

compounds having three carbon atoms:

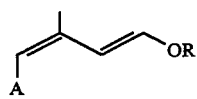

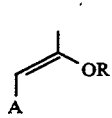

and compounds having 2 carbon atoms:

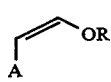

The process for preparing the compounds of formula (III) consists in carrying out thermal cracking of acetals of the formula (V):

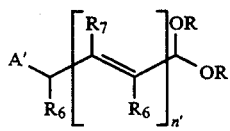

(V)

in which A, $R_7$, $R_6$, R and n' have the same meaning as above.

The cracking can be performed in the presence of a catalytic amount of an acid chosen from: p-toluenesulphonic acid, toluic acid, zinc chloride or heterogeneous acid catalysts and the like.

Converting the compounds of formula I to Vitamin A, when A represents a halogen atom, comprises dehydro-halogenating the molecule of formula (I) or (II) obtained. This step is performed in accordance with the teaching of the publication by Oediger, Kabbe, Moller and Eiter which appeared in *Chem. Ber.* 99(6):2012–2016 (1966).

The dehydrohalogenating agent is chosen in particular from:
lithium chloride in dimethylformamide,
diazabicyclooctane (DABCO),
diazabicyclononene (DBN),
diazabicycloundecene (DBU),
quinuclidine,
potassium hydroxide or sodium hydroxide in a hydrocarbon, optionally in the presence of a phase transfer agent, and metallic palladium in the presence of a base.

When A represents a sulphinyl group it is advantageous to dissolve the compound of formula (I) or (II) in carbon tetrachloride.

The present invention will be more completely described by the following examples which should not be considered as limiting the invention.

EXAMPLE 1

Preparation of the Compound of Formula [IV]

1) Cracking of brominated acetal

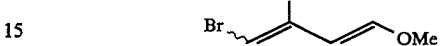

8 grams of 1-bromo-2-methyl-4,4-dimethoxy-2-butene (38.28 mmol) were introduced into a distillation apparatus. The product was heated, with stirring, at atmospheric pressure, until fumes appeared over the supernatant. The heating was then stopped and the mixture was placed under a water jet vacuum. A mixture of the starting acetal and the expected enol ether was thus distilled. The latter was purified by flash chromatography on silica and 1.7 g thereof were obtained. Yield=25%.

2) Cracking of chlorinated acetal

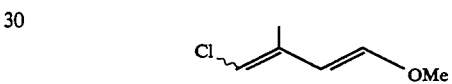

10 grams of 1-chloro-2-methyl-4,4-dimethoxy-2-butene (60.8 mmol) were introduced into a distillation apparatus. The product was heated until distillation of the methanol was complete. 7.6 g of chlorinated enol ether were then distilled under a water jet vacuum (yield 94%).

3. Formation and cracking of phenylthioacetal

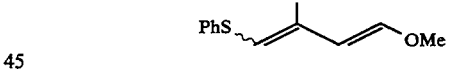

20 grams of 1-chloro-2-methyl-4,4-dimethoxy-2-butene (0.122 mol) were introduced into 68 ml of triethylamine and 14 g of thiophenol (or 1 equiv.) in solution and 65 ml of ether were added dropwise using a dropping funnel, over 10 min at room temperature. The mixture was kept stirring at this temperature for 15 hours, filtered and the triethylamine hydrochloride was washed with 30 ml of ether. The ether phases were concentrated and then the residue was placed in a distillation apparatus. It was heated until distillation of the methanol was complete and then 20 g of 1-methoxy-3-methyl-4-phenylthio-1,3-butadiene were distilled. The yield relative to the starting chloroacetal was 80%. b.p.$_{0.5}$ $_{mmHg}$=129° C.

4) Formation and cracking of phenylselenoacetal
The following reaction was used:

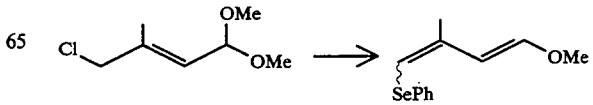

3.1 g (2.1 equiv.) of sodium borohydride were added in small fractions, at 0° C. and under argon, to a solution of 12 grams (38.5 mmol) of diphenyl diselenide in 200 ml of ethanol. The reaction was exothermic.

The mixture was kept stirring until the evolution of hydrogen ceased, and then 12.7 g (2 equiv.) of 1-chloro-2-methyl-4,4-dimethoxy-2-butene were added dropwise. After stirring for 15 hours at room temperature, the mixture was filtered and concentrated and the NaCl residue was crystallized from petroleum ether. Then the crude product was introduced into a distillation assembly. The cracking began at around 120° C. and 12.7 g of the expected enol phenylselenoether were distilled at 150° C. under 0.6 mmHg: the yield was 65%.

5) Formation and cracking of $C_2$ phenylthioacetal

The following reaction was used:

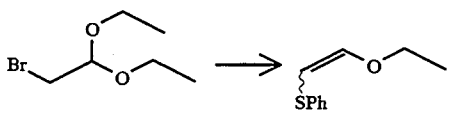

5.75 g of sodium metal (0.25 mmol) were added to 200 ml of absolute ethanol and allowed to dissolve completely. 27.5 g (0.25 mol) of thiophenol were added dropwise followed by 38 ml of 1-bromo-2,2-diethoxyethane (1 equiv.); the mixture was refluxed for 2 hours, the solution was poured into 500 ml of water and then extracted from chloroform and dried over $MgSO_4$. The crude product was introduced into a distillation assembly. The cracking began at around 120° C., and then the expected enol ether was distilled. The yield was 30%.

6) Formation and cracking of $C_5$ acetoxyacetal

1-Acetoxy-4,4-dimethoxy-2-methyl-2-butene

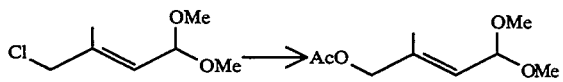

A solution of 30 g of $C_5$ chloroacetal (0.182 mol) and 18 g of potassium acetate (1 equiv.) in 75 ml of methanol was refluxed for 24 hours. The mixture was then allowed to return to room temperature, was concentrated, taken up in 100 ml of ether, washed 2 times with 30 ml of water, dried over magnesium sulphate, filtered and concentrated. The yield was 65%.

1-Acetoxy-4-methoxy-2-methyl-1,3-butadiene

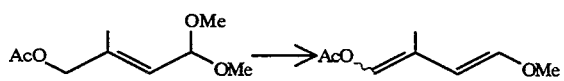

The crude acetal was placed in a Claisen apparatus and then heated to not less than 120° C., the temperature at which cracking appeared to take place. The expected enol ether was then distilled. The yield was 50% (mass obtained: 17 g). b.p.$_{0.4}$ mmHG=75°-82° C. Two isomers were present in 50/50 proportions.

EXAMPLE 2

Preparation of the Compound of Formula I (A=SPh, n=2, m=0, R'=bond to chain)

1) Reaction of enol phenylthioether on vinyl beta-ionol in the presence of boron trifluoride etherate

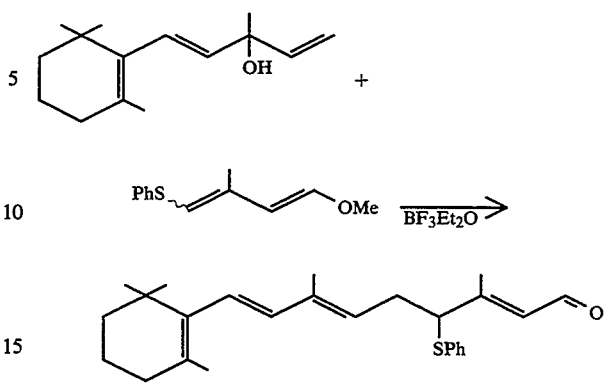

0.61 g of enol phenylthioether 2.96 mmol) in 3 ml of nitroethane was introduced into a two-necked flask previously purged with argon. The mixture was cooled to −35° C. and then a solution of 0.66 g of vinyl beta-ionol (1 equiv.) in 3 ml of nitroethane was added at this temperature over 2 min using a push syringe; the mixture was kept stirring for 10 min and then 75 μl of boron trifluoride etherate (0.2 equiv.) were rapidly added. The solution became green. It was kept stirring between −30° and −35° C. for one hour and then 4.5 ml of saturated aqueous solution of sodium bicarbonate were rapidly added. The mixture was allowed to return to room temperature and then it was stirred for 15 min. 5 ml of dichloromethane were added and then the organic phase was washed 2 times with 5 ml of water. The organic phase was dried over magnesium sulphate, filtered, concentrated and the crude product was chromatographed on silica. 580 mg of phenylthioretinal, equivalent to a yield of 50%, were thus recovered.

2) Preparation of Vitamin A Acetate a) Reduction of Phenylthioretinal to an Alcohol with Sodium Borohydride The following reaction was used:

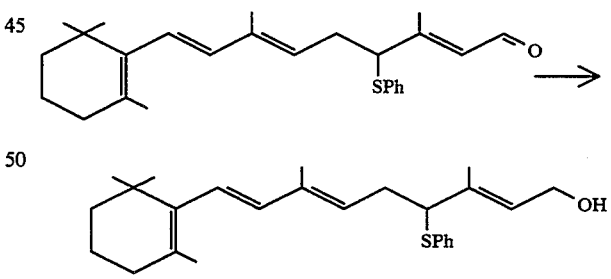

55 mg of sodium borohydride (1.45 mmol) were added to a solution of 0.57 g of the above $C_{20}$ aldehyde (1.45 mmol) in 6 ml of methanol and then the mixture was allowed to return to room temperature over 15 min. It was kept stirring overnight (about 15 hours) and then 15 ml of water were added and the mixture was extracted [with] 2 times with 10 ml of ether, washed with 10 ml of water, dried over magnesium sulphate, filtered and concentrated to recover 0.57 g of alcohol, equivalent to a yield of 99.5%.

b) Acylation of the Alcohol to an Acetate

The following reaction was used:

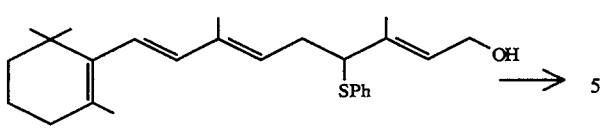

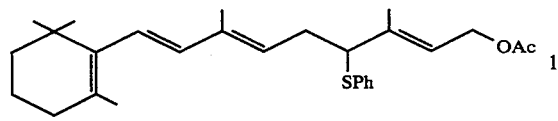

0.21 ml of triethylamine (1.5 mmol; 1.6 equiv.) and 0.17 ml of acetic anhydride (1.8 mmol; 1.9 equiv.) were successively introduced into a solution of 0.37 g of the C$_{20}$ alcohol (0.93 mmol) in 9 ml of hexane. After stirring for 7 hours at 40° C., complete disappearance of the initial alcohol spot was observed during TLC. 7 ml of ice cold water were then added and then the mixture was taken up in 5 ml of ether and washed with 5 ml of water. The product was dried over magnesium sulphate, filtered and concentrated in order to recover 405 mg of C$_{20}$ acetate. The yield was quantitative.

c) Oxidation of the Acetate

The following reaction was used:

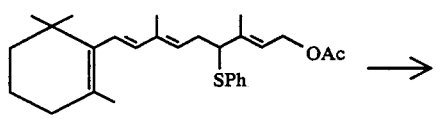

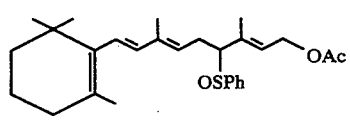

0.206 g (1.15 equiv.) of meta-chloro-perbenzoic acid in 2.5 ml of dichloromethane were poured into a solution of 0.455 g (1.04 mmol) of the above acetate in 10 ml of dichloromethane, cooled to 0° C.

The reaction was complete after 1 hour at 0° C. The mixture was hydrolysed by rapidly adding 5 ml of a saturated aqueous solution of sodium bicarbonate, the two phases were separated and the organic phase was washed 2 times with 15 ml of normal sodium hydroxide, dried over magnesium sulphate, filtered and concentrated. The crude yield was 100%.

d) Dehydrosulphoxidation on the Acetate: Preparation of Vitamin A Acetate

The following reaction was used:

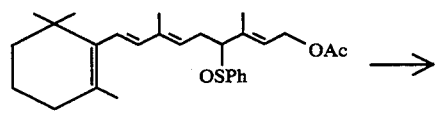

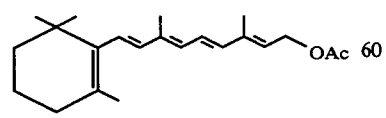

0.51 g of the above C$_{20}$ phenyl sulphoxide (1.12 mmol) was placed in 4 ml of carbon tetrachloride and the solution was heated to reflux temperature. It took 3 h 30 min for the sulphoxide to disappear during TLC. The residue was concentrated and then chromatographed on activated alumina II (eluent: petroleum ether/Et$_2$O=97/3). 0.28 g of vitamin A acetate was thus recovered. The yield was 76%.

3) Preparation of Retinal a) Oxidation of the Aldehyde

The following reaction was used:

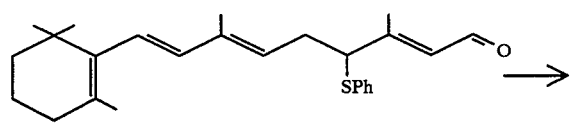

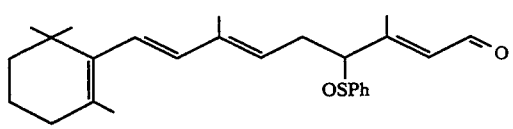

1.15 equiv. of meta-chloroperbenzoic acid in 2.5 ml of dichloromethane were poured into a solution of 0.41 g (1.04 mmol) of phenythioretinal in 10 ml of dichloromethane, and cooled to 0° C.

The reaction was complete after 1 hour at 0° C. 5 ml of a saturated aqueous solution of sodium hydrogen carbonate were rapidly added, the two phases were separated and the organic phase was washed 2 times with 15 ml of 1 normal sodium hydroxide, dried over magnesium sulphate, filtered and concentrated. The crude yield was 100%.

b) Dehydrosulphoxidation on the Aldehyde: Preparation of the Retinal

The following reaction was used:

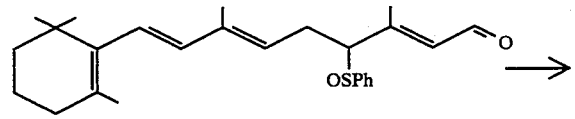

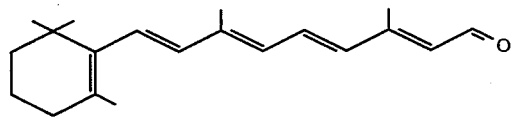

0.43 g of C$_{20}$ phenyl sulphoxyaldehyde (1.05 mmol) was placed in 8 ml of carbon tetrachloride and the disappearance of the sulphoxide was monitored by TLC. The reaction appeared to be instantaneous at room temperature. After 1 hour, the residue was concentrated and chromatographed on silica (eluent: petroleum ether/Et$_2$O=95/5). 0.275 g of retinal was thus recovered. The yield was 92%.

EXAMPLE 3

Preparation of the Compound of Formula (I) (A=Cl, n=2, m=1, R=bond to chain)

1) Synthesis and Application of a Retinal Derivative

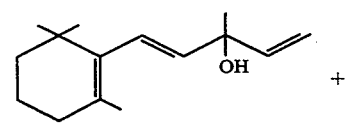

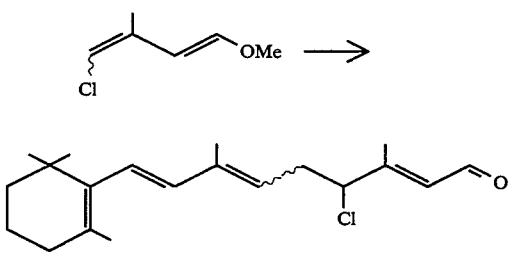

a) Standard Conditions 0.41 g of chlorinated enol ether and 0.66 g of vinyl β-ional (equivalent to 3 mmol of each) were mixed at room temperature with 6 ml of nitroethane. The solution was cooled to −35° C. in a thermostated bath and the catalyst (0.5 equiv. of zinc chloride or 0.2 equiv. of boron trifluoride etherate) was rapidly added. After stirring for 10 min at −35° C., 5 ml of saturated aqueous solution of sodium bicarbonate were rapidly added and then the mixture was allowed to return to room temperature over 10 min. The mixture was extracted 2 times with 5 ml of dichloromethane and then washed with 5 ml of water. It was dried over magnesium sulphate, filtered and concentrated. 0.400 g of the $C_{20}$ chlorinated aldehyde, equivalent to a yield of 42%, was recovered after flash chromatography on silica (petroleum ether-/ethyl ether: 96/4). The compound obtained was analyzed by NMR and infrared spectrophotometry.

b) Common Conditions for Tables 1-1 to 1-8

The 2 reagents were introduced into the solvent in equimolar quantities (unless otherwise stated) at a concentration of 0.5M. The reaction medium was adjusted to the temperature indicated and then the catalyst was added and the mixture was allowed to react for the time indicated.

1-1) Influence of the Catalyst
Common conditions: 1 equiv. of isopropanol, 10 min at −35° C. in nitroethane

| CATALYST | QUANTITY | YIELD |
| --- | --- | --- |
| $CF_3SO_3H$ | 0.2 equiv. | 47% |
| $CF_3SO_3SiMe_3$ | 0.2 equiv. | 46% |
| $CF_3SO_3SiMe_2tBu$ | 0.2 equiv. | 36% |
| $SbCl_3$ | 0.2 equiv. | 34% |
| $SnCl_4$ | 0.2 equiv. | 30% |
| $CF_3COOH$ | 0.2 equiv. | 25% |
| HCOOH | solvent | 22% |
| $SnCl_2$ | 0.2 equiv. | 20% |
| $BiCl_3$ | 0.2 equiv. | 16% |

1-2) Influence of the Temperature
Common conditions: one hour in nitroethane.

| CATALYST | TEMP. IN °C. | YIELD |
| --- | --- | --- |
| 0.2 equiv. $BF_3$—$Et_2O$ | −45 | 31% |
| Idem | −35 | 32% |
| Idem | −20 | 25% |
| Idem | 0 | 25% |
| 0.2 equiv. $ZnCl_2$ | 0 | 27% |
| Idem | −35 | 35% |

1-3) Influence of the Time
Common conditions: temperature of −35° C. nitroethane solvent.

| CATALYST | TIME IN MIN | YIELD |
| --- | --- | --- |
| 0.5 equiv. $ZnCl_2$ | 5 | 40% |
| Idem | 10 | 42% |
| Idem | 15 | 28% |
| Idem | 60 | 12% |
| 0.2 equiv. $BF_3Et_2O$ | 60 | 32% |
| Idem | 10 | 41% |

This table shows, in a general manner, that the reaction is very rapid.

1-4) Nature of the Solvent and the Concentration
Common conditions: 10 min at −35° C.: 0.5 equiv. of zinc chloride.

| SOLVENT | CONCENTRATION | YIELD |
| --- | --- | --- |
| $EtNO_2$ | 0.5M | 42% |
| $EtNO_2$ | 1M | 35% |
| $CH_2Cl_2$ | 0.5M | 21% |

1-5) Influence of the Addition of alcohol
Common conditions: 0.5 equiv. of zinc chloride, 10 min at −35° C. in dichloromethane.

| ALCOHOL | YIELD |
| --- | --- |
| Without | 42% |
| Isopropanol | 53% |
| Tert-butanol | 51% |
| 2-Pentanol | 43% |
| Isobutanol | 38% |

1-6) Influence of the Addition of a Protic Acid
Common conditions: carboxylic acid/water mixture, 5/1 vol/vol. used as solvent

| CATALYST | TEMP. °C. | DURATION | YIELD |
| --- | --- | --- | --- |
| HCOOH | −15° C. | 15′ | 60% |
| $CCl_3COOH$ | −15° C. | 3′ | 30% |
| $CF_3COOH$ | −25° C. | 0.5′ | 18% |

1-7 Hydrolysing Agent
Two different hydrolysing agents were used after condensation under the same conditions: 10 min at −35° C. in nitroethane: 0.5 equiv. of zinc chloride.

| HYDROLYSING AGENT | YIELD |
| --- | --- |
| Sat. $NaHCO_3/H_2O$ (excess) | 42% |
| Triethylamine (0.5 equiv.) | 40% |

1-8) Respective Proportions of the Reagents
20 minutes at −35° C. in nitroethane; 0.5 equiv. of zinc chloride.

| ENOL ETHER | VINYL β-IONOL | YIELD |
| --- | --- | --- |
| 1 | 1 | 42% |
| 2 | 1 | 42% |
| 1 | 2 | 15% |

1-9) Stereochemistry

High-field NMR analysis shows that the C20 chlorinated aldehyde is a mixture of the following steroisomers:

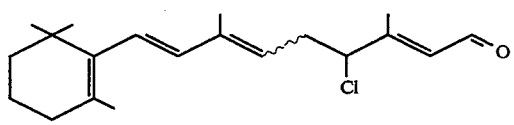

All-trans: 65%
7-trans, 9-cis, 13-trans: 35%

2) Application to the Preparation of Vitamin A a) Dehydrochlorination of the Aldehyde Using Lithium Chloride

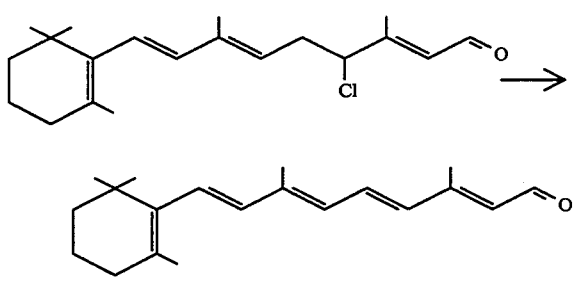

A mixture of 125 mg (0.39 mmol) of $C_{20}$ chlorinated aldehyde and 60 mg (or 3 equiv.) of dry lithium chloride in 6 ml of anhydrous dimethylformamide was heated to 100° C. After 10 min at 100° C., disappearance of the starting material was observed during thin-layer chromatography. The solution was allowed to return to room temperature over 10 min and then 50 ml of ether were added and the mixture was washed 2 times with 20 ml of water and 2 times with 20 ml of saturated aqueous solution of sodium bicarbonate. It was dried over magnesium sulphate, filtered and concentrated. The crude product was chromatographed on silica (petroleum ether/ethyl ether: 98/2) and 83 mg of retinal, equivalent to a yield of 75%, were recovered.

HPLC analysis: $\lambda=330$ nm; flow rate—1.5 ml/min; P=70 bars; eluent: hexane/ethyl ether=9/1 All-trans: 44.9% 9-cis: 16.8% 13-cis: 38.3%.

b) Dehydrochlorination of the Aldehyde with Diazabicycloundecene (DBU)

0.13 ml (or 1.05 equiv.) of DBU was rapidly added at room temperature to a solution of 270 mg of $C_{20}$ chlorinated aldehyde in 1.5 ml of dichloromethane and the mixture was kept stirring at this temperature for 24 hours. The dichloromethane was evaporated and the residue was taken up in 10 ml of ether, washed 2 times with 5 ml of a saturated aqueous solution of sodium bicarbonate, then with 5 ml of water and then dried over magnesium sulphate, filtered and concentrated. The crude product was chromatographed on silica (petroleum ether/ethylene ether: 98/2), and 203 mg of retinal were recovered. Yield 85%.

HPLC analysis: $\lambda=330$ nm; flow rate=1.5 ml/nm; P=70 bars; eluent: hexane/ether=9/1 All-trans: 58.7% 9-cis: 7.7% 13-cis: 33.6%.

c) Dehydrochlorination Using a Mixture of $PdCl_2$, $P(C_6H_5)_3$ $PdCl_2$ (5.4 mg; 0.032 mmol) and $P(C_6H_5)_3$ (20.3 mg; 0.77 mmol) were added, under argon at 60° C., to a solution of $C_{20}$ chlorinated aldehyde (99 mg; 0.31 mmol) and triethylamine (47 mg; 0.46 mmol) in 2 ml of dimethylformamide. The mixture was kept stirring at 60° C. for 2 hours. It was extracted in the same manner as in Example 2. The retinal was obtained with a yield of 78%.

d) Reduction of the Chlorinated Aldehyde to an Alcohol

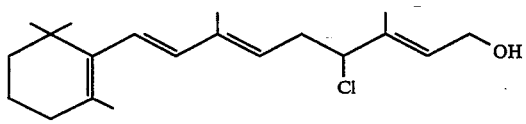

30 mg of sodium borohydride were added, at 0° C. over 1 min, to a solution of 250 mg (0.78 mmol) of $C_{20}$ chlorinated aldehyde in 10 ml of the THF and then the mixture was kept stirring at 0° C. for 5 hours. 5 ml of water were then added and the mixture was extracted 2 times with 10 ml of ether, washed with 10 ml of water, dried over magnesium sulphate, filtered and concentrated: 250 mg of chlorinated alcohol, equivalent to a yield of 99%, are recovered.

IR (film, $cm^{-1}$): 3400, 2940, 2905, 2850; 1445; 1370.

e) Acylation of the alcohol to an acetate

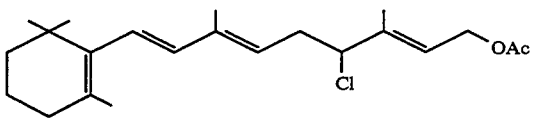

0.21 ml of triethylamine and 0.17 ml of acetic anhydride were successively added to a solution of 250 mg of the above-obtained chlorinated alcohol in 9 ml of hexane. The mixture was allowed to react for 15 hours at room temperature and then for 2 hours at 40° C. to give 268 mg of $C_{20}$ chlorinated acetate, equivalent to a yield of 95%.

f) Dehydrochlorination of the Acetate Using Diazabicyclononene (DBN)

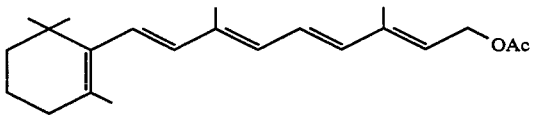

A solution of 1 g of diazabicyclononene (DBN) (or 2 equiv.) in 3 ml of toluene was rapidly added to a solution of 1.5 g (4.12 mmol) of $C_{20}$ chlorinated acetate in 3 ml of toluene. The mixture was heated at 80° C. for 15 min and then allowed to cool and poured onto 10 g of ice containing 1 ml of a molar aqueous solution of sulphuric acid. It was extracted 3 times with 10 ml of petroleum ether, washed with 10 ml of a saturated aqueous solution of sodium hydrogen carbonate, dried over magnesium sulphate, filtered and concentrated to give 1.29 g of vitamin A acetate, equivalent to a yield of 99.5%.

HPLC analysis: $\gamma=280$ nm; flow rate=1.5 ml/min; P=70 bars; eluent: hexane/ether=97/3 All-trans: 79.6% 9-cis: 12% 13-cis: 8.4%.

EXAMPLE 4

Production of a Compound of Formula I (A=SePh, n=2, m=1, R=bond to chain) by the action of a $C_5$ enol phenylselenoether on vinyl $\beta$-ional:

1) Preparation of Phenylselenoretinal

The following reaction was used:

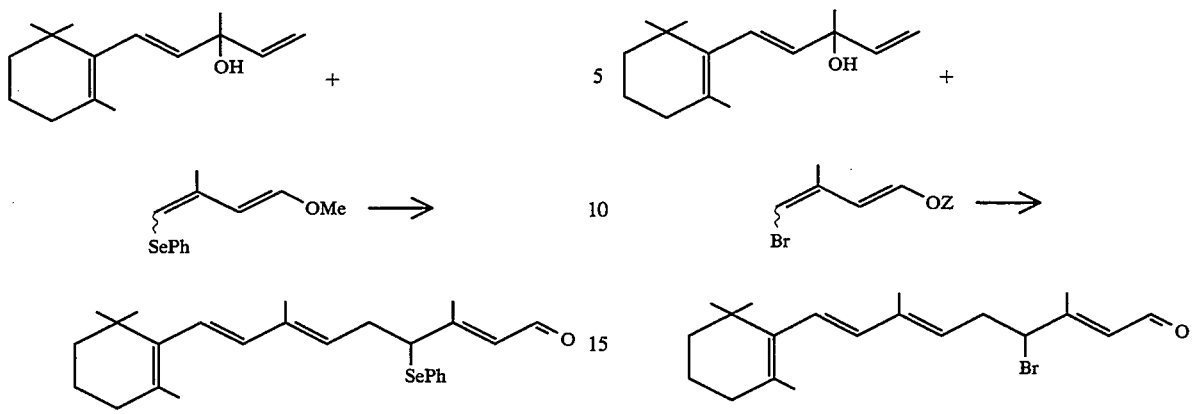

5 ml of formic acid and 1 ml of water, previously cooled to 0° C., were added to a mixture of 0.660 g (3 mmol) of vinyl β-ionol and 0.855 g (1 equiv.) of enol ether, previously cooled to 0° C. The mixture was allowed to react for 60 min at 0° C. and then 3 ml of pentane were added and the pentane phase was washed 2 times with 1.5 ml of water. The pentane phase was dried over MgSO₄ and then filtered and concentrated: the expected product was purified by flash chromatography on silica (eluent: pet. eth./Et₂O=96/4): the yield was 48%.

2) Preparation of the Retinal

The following reaction was used

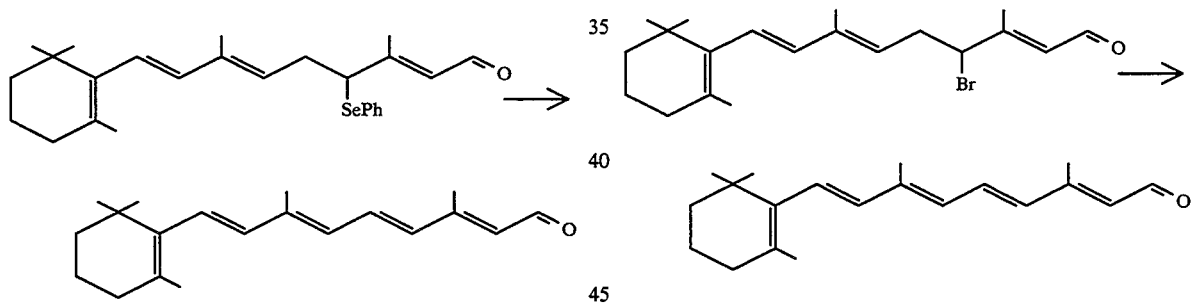

210 mg (1.1 equiv.) of meta-chloroperbenzoic acid in solution in 5 ml of dichloromethane were added, at 0° C. to a solution of 0.500 g (1.113 mmol) of derivative I (A=SePh) in solution in 10 ml of dichloromethane. The formation of the retinal was instantaneous. It was immediately treated with 5 ml of an aqueous solution of sodium bicarbonate, extracted with 5 ml of dichloromethane, washed 2 times with 3 ml of 0.5N sodium hydroxide, dried over magnesium sulphate, filtered and concentrated. The yield of retinal, purified by flash chromatography on silica (eluent: pet. eth./Et₂O=96/4), was 90%.

EXAMPLE 5

Production of a Compound of Formula I (A=Br, n=2, m=1, R=bond to chain) by the action of a C₅ enol bromoether on vinyl β-ional 1) Preparation of Bromoretinal The following reaction was used where Z=Et or SiMe₃:

5 ml of formic acid and 1 mol of water, previously cooled to −10° C., were added to a mixture of 0.660 g (3 mmol) of vinyl β-ional and 3 mmol (1 equiv.) of the enol ether, previously cooled to −10° C. The mixture was allowed to react for 60 min at −10° C. and then 3 ml of pentane were added and the pentane phase was washed 2 times with 1.5 ml of water. It was dried over MgSO₄ and then filtered and concentrated: the expected product was purified by flash chromatography on silica (eluent: pet. eth./Et₂O=94/4). The yield was 32% for Z=Et, and 28% for Z=SiMe₃.

2) Preparation of the Retinal The following reaction was used:

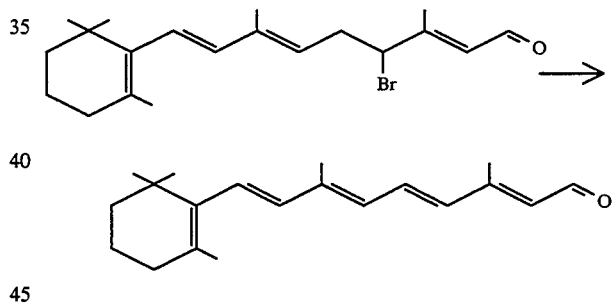

0.22 g (0.6 mmol) of hydrobrominated retinal was placed in 3 ml of dichloromethane and then 92 microliters (1 equiv.) of DBU were added. The mixture was kept stirring for 1 hour and then concentrated and taken up in 5 ml of ether, washed 2 times with 3 ml of water, dried over magnesium sulphate, filtered and concentrated to yield 0.165 g of retinal.

Yield=96.5%.

EXAMPLE 6

Production of a Compound of Formula I A=Br, n=3, m=0, R=bond to chain) by the action of a C₂ enol ether on a C₁₈ derivative Preparation of Brominated C₂₀ Aldehyde The following reaction was used:

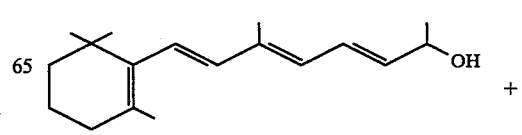

-continued

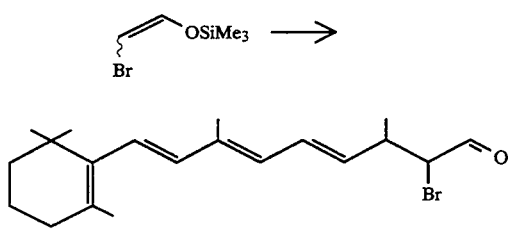

933 mg (3.6 mmol) of a $C_{18}$ alcohol and 3.6 mmol. (1 equiv.) of 1-bromo-2-trimethylsiloxy-ethylene were placed in 7.2 ml of nitroethane, cooled to −35° C., and 90 microliters of boron trifluoride etherate were added. The mixture was kept stirring for 1 hour at −35° C. and it was then hydrolysed with 6 ml of an aqueous solution of sodium bicarbonate and extracted with dichloromethane.

The expected product was characterized by $^1$H NMR. $^1$H NMR (CDCl$_3$): 9.35 (d, 1H, J=8.75 Hz).

The $C_{18}$ alcohol was obtained by the action of lithium aluminium hydride on the $C_{18}$ ketone in anhydrous ether at 0° C.

EXAMPLE 7

Process for Preparing the Retinal by the Action of a $C_5$ Enol Acyloxyether on Vinyl β-ional 1) Preparation of Acyloxy Retinal The following reaction is used wherein Z=methyl or SiMe$_3$:

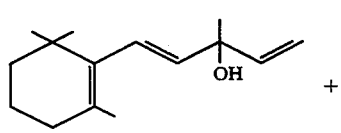

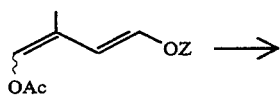

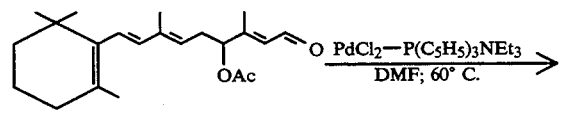

5 ml of formic acid and 1 ml of water, previously cooled to 0° C., were added to a mixture of 660 mg (3 mmol) of vinyl β-ional and 3 mmol (1 equiv.) of enol ether, previously cooled to 0° C. The mixture was allowed to react for 30 min at 0° C. and then 5 ml of pentane were added and the pentane phase was washed 2 times with 1.5 ml of water. The pentane phase was dried over MgSO$_4$ and then filtered and concentrated: the expected product was purified by flash chromatography on silica (eluent: pet. eth./Et$_2$O=93/7). The yield was 45% for Z=SiMe$_3$ and 39% for Z=Me.

2) Preparation of the Retinal

The following reaction was used:

-continued

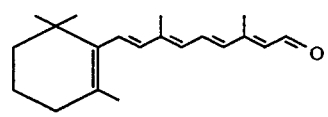

The procedure was identical to that in Example 3. The yield of retinal, purified by flash chromatography on silica, was 55%.

EXAMPLE 8

Process for Preparing a Dihydroretinal by the Action of a $C_5$ Enol Derivative on Vinyl β-ional The following reaction was used:

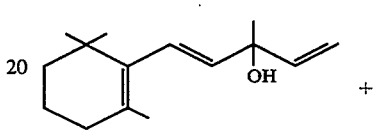

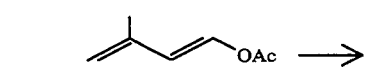

5 ml of formic acid and 1 ml of water were added to a mixture of 660 mg (3 mmol) of vinyl β-ionol and 380 mg of enol acetate (3 mmol). The mixture was allowed to react for 60 min at 20° C. and then 3 ml of pentane were added and the pentane phase was washed 2 times with 1.5 ml of water. It was dried over MgSO$_4$ and then filtered and concentrated. The expected product was purified by flash chromatography on silica (eluent: pet. eth./Et$_2$O=96/4). The yield was 47%.

EXAMPLE 9

Process for Preparing a Dihydroretinal by the Action of a $C_5$ Trimethylsilated enol ether on vinyl β-ionol The following reaction was used:

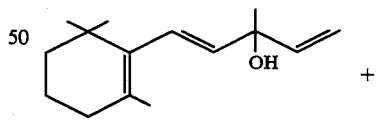

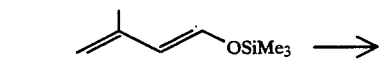

5 ml of formic acid and 1 ml of water, previously cooled to −10° C., were added to a mixture of 660 mg (3 mmol) of vinyl β-ional and 470 mg of enol ether (3 mmol), previously cooled to −10° C. and then 3 ml of pentane were added and the pentane phase was washed

EXAMPLE 10

Process for Preparing a Dihydroretinal by the Action of a $C_7$ Enol Ether β-ionol The following reaction was used:

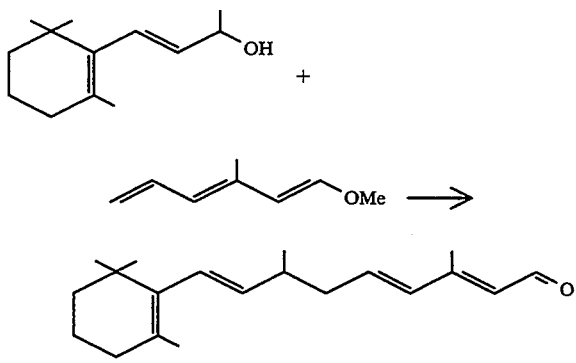

190 μl of boron trifluoride etherate (or 0.4 equiv.) were rapidly added to a solution of 580 mg (3 mmol) of β-ionol and 370 mg (3 mmol) of enol ether in 6 ml of nitroethane, cooled to −20° C., and the mixture was kept stirring at this temperature for 1 h 30 min. It was hydrolysed with 5 ml of a saturated aqueous solution of sodium bicarbonate. The mixture was extracted 2 times with 5 ml of pentane and the pentane phase was washed 2 times with 1.5 ml of water, dried over MgSO4 and then filtered and concentrated. The expected product was purified by flash chromatography on silica (eluent: pet. eth./Et2O=96.4). The yield was 41%.

EXAMPLE 11

Production of a $C_{18}$ Compound of Formula I (A=SPh, n=2, m=0, R'=bond to chain) by the action of a $C_{33}$ enol ether on vinyl β-ionol 1) Preparation of Phenylthio $C_{18}$ Ketone The following reaction was used:

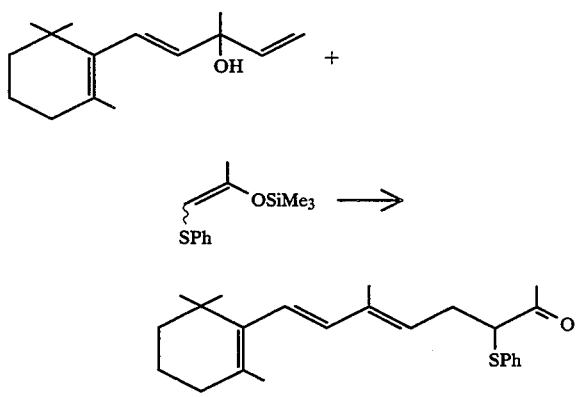

5 ml of formic acid and 1 ml of water, previously cooled to 0° C., were added to a mixture of 660 mg (3 mmol) of vinyl β-ionol and 710 mg of enol ether (3 mmol), previously cooled to 0° C. The mixture was allowed to react for 30 min at 0° C. and then 3 mol of pentane were added. The pentane phase was washed 2 times with 1.5 ml of water, then dried over MgSo4, filtered and concentrated: the expected product was purified by flash chromatography on silica (eluent: pet. eth./Et2O=96/4). The yield was 28%.

2) Preparation of the $C_{18}$ Ketone

The following reaction was used:

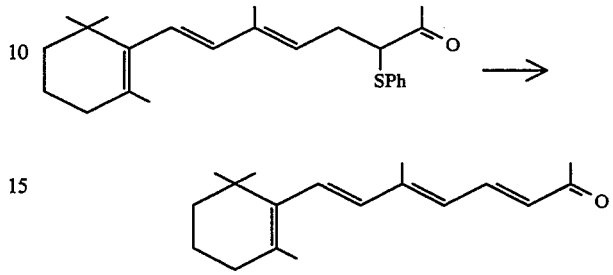

The procedure for the oxidation was the same as that described in Example 2. 0.15 g of phenylthioketone (0.41 mmol) and meta-chloroperbenzoic acid were used as starting materials.

The crude product was taken up in 3 ml of carbon tetrachloride and the solution was heated to 60° C. for 2 hours. It was concentrated and chromatographed on silica to give 70 mg of $C_{18}$ ketone (eluent: pet. eth. Et2O=96/4). The yield was 67%.

EXAMPLE 12

Production of a $C_{18}$ Compound of Formula I (A=Br, n=2, m=0, R'=bond to chain) by the action of a $C_3$ enol ether on vinyl β-ionol 1) Preparation of Brominated $C_{18}$ Ketone The following reaction was used:

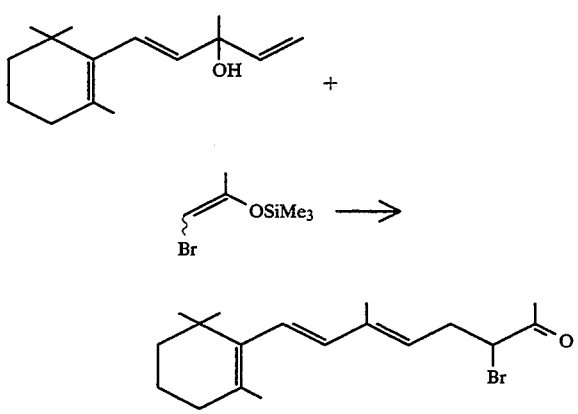

5 ml of formic acid and 1 ml of water, previously cooled to −10° C., were added to a mixture of 660 mg (3 mmol) of vinyl β-ionol and 630 mg (3 mmol) of enol ether, previously cooled to −10° C. The mixture was allowed to react for 30 min at −10° C. and then 3 ml of pentane were added and the pentane phase was washed 2 times with 1.5 ml of water. It was dried over MgSo4 and then filtered and concentrated. The expected product was purified by flash chromatography on silica (eluent: pet. eth./Et2O=96/4). The yield was 54%.

2) Preparation of the $C_{18}$ Ketone

The following reaction was used:

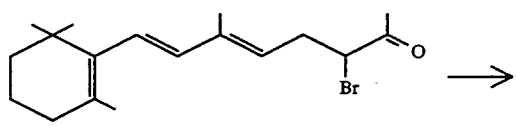

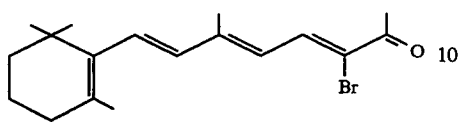

0.5 g of brominated $C_{18}$ (1.47 mmol) was placed in 4 ml of dichloromethane and then 0.225 ml of DBU (1 equiv.) was added. The mixture was kept stirring for 1 hour and then concentrated and taken up in 5 ml of ether, washed 2 times with 3 ml of water, dried over magnesium sulphate, filtered and concentrated to give 220 mg of $C_{18}$ ketone.
The yield was 58%.

EXAMPLE 13

Production of $C_{18}$ Compound of Formula I (A=Cl, n=2, m=0, R'=bond to chain) by the action of a $C_3$ enol on vinyl β-ionol 1) Preparation of Chlorinated $C_{18}$ Ketone
The following reaction was used:

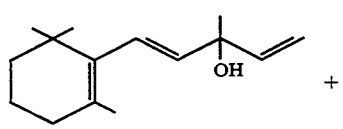

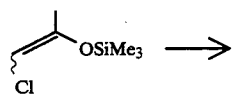

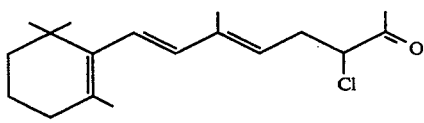

5 ml of formic acid and 1 ml of water, previously cooled to −10° C., were added to a mixture of 660 mg (3 mmol) of vinyl β-ionol and 500 mg (3 mmol) of enol ether, previously cooled to −10° C. The mixture was allowed to react for 30 min at −10° C. and then 3 ml of pentane were added and the pentane phase was washed 2 times with 1.5 ml of water. It dried over MGSO4 and then filtered and concentrated: the expected product was purified by flash chromatography on silica (eluent: pet. eth./Et2O=96/4). The yield was 54%.

2) Preparation of the $C_{18}$ Ketone
The following reaction was used:

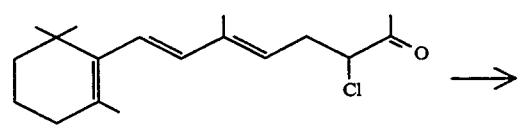

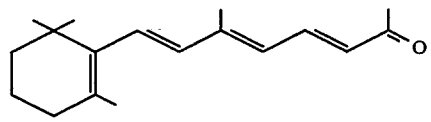

0.45 g of chlorinated $C_{18}$ (1.53 mmol) was placed in 3 ml of dichloromethane and then 0.235 ml of DBU (1 equiv.) was added. The mixture was kept stirring for 15 hours and then concentrated and taken up in 5 ml of ether, washed 2 times with 3 ml of water, dried over magnesium sulphate, filtered and concentrated to give 330 mg of $C_{18}$ ketone. The yield was 84%.

EXAMPLE 14

Process for Preparing a $C_{18}$ Compound by the Action of a $C_3$ Enol Ether on Vinyl β-ionol
The following reaction was used:

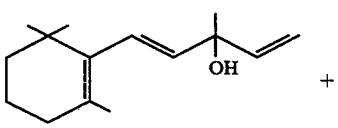

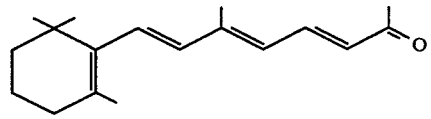

5 ml of formic acid and 1 ml of water were added to a mixture of 660 mg (3 mmol) of vinyl β-ionol and 390 mg (3 mmol) of enol ether. The mixture was allowed to react for 30 min at 20° C. and then 3 ml of pentane were added and the pentane phase was washed 2 times with 1.5 ml of water. It was dried over MgSO4 and then filtered and concentrated. The expected product was purified by flash chromatography on silica (eluent: pet. eth/Et2O=06/4). The yield was 42%.

EXAMPLE 15

Production of a $C_{17}$ Compound of Formula I (A=Br, n=2, m=O, R'=bond to chain) by the action of a $C_2$ enol bromoether on vinyl β-ionol
The following reaction was used:

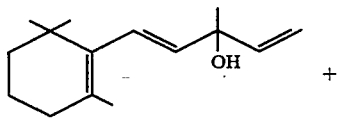

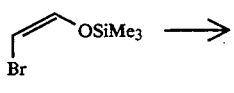

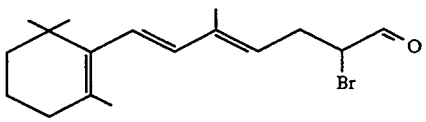

0.66 g (3 mmol) of vinyl β-ionol and 585 mg (1 equiv.) of 1-bromo-2-trimethylsilyloxyethylene were placed in 10 ml of nitroethane, cooled 30°–35° C., and 190 microliters of boron trifluoride etherate were added. The mixture was kept stirring for 1 hour at −35° C. and then hydrolysed with 6 ml of an aqueous solution of sodium bicarbonate and extracted with dichloromethane.

The expected product was characterized by $^1$H NMR. $^1$H NMR (CDCl$_3$): 9.5 (D,1H,J - 6.4 Hz).

EXAMPLE 16

Production of C$_{15}$ Compound of Formula I (A=SPh, n=1, m=0, R'=bond to chain) by the action of a C$_2$ enol ether on β-ionol 1) Preparation of Thiophenol of C$_{15}$ Aldehyde The following reaction was used:

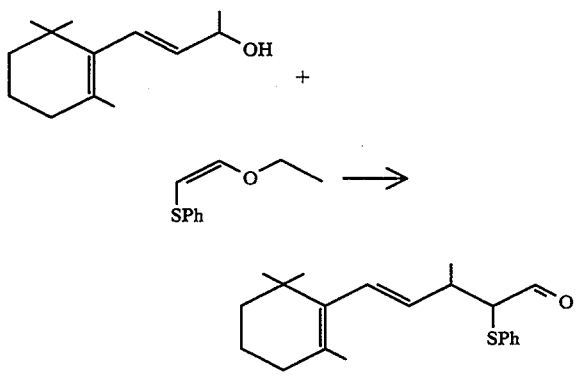

190 μl (or 0.4 equiv.) of boron trifluoride etherate were rapidly added to a solution of 580 mg (3 mmol) of β-ionol and 500 mg (3 mmol) of enol ether in 6 ml of nitroethane, cooled to −20° C., and the mixture was kept stirring at this temperature of 1 h 30 min. It was hydrolysed with 5 ml of a saturated aqueous solution of sodium bicarbonate. The mixture was extracted 2 times with 5 ml of pentane and the pentane phase was washed 2 times with 1.5 ml of water. It was dried over MgSo$_4$ and then filtered and concentrated: the expected product was purified by flash chromatography on silica (eluent: pet. eth./Et$_2$O - 96/4). The yield was 63%.

2) Preparation of the C$_{15}$ Aldehyde (β-ionylideneacetaldehyde)

The following reaction was used:

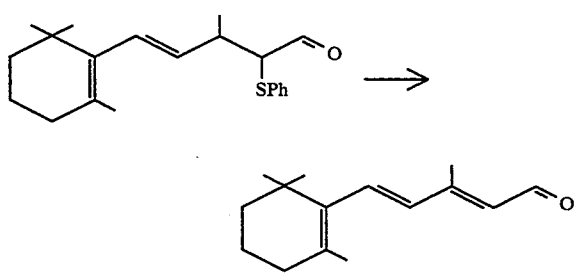

The procedure for the oxidation was the same as that described above in Example 2. 0.15 g (0.46 mmol) of the above aldehyde and 87 mg (0.51 mmol; 1.1 equiv.) of metachlorperbenzoic acid were used as starting material.

The crude material was taken up in 4 ml of carbon tetrachloride and the solution was heated at 60° C. for 1 hour. It was concentrated and taken up in 3 ml of ether, washed with water, dried over magnesium sulphate, filtered and concentrated. The C$_{15}$ aldehyde was detected by $^1$H NMR.

EXAMPLE 17

Production of a C$_{15}$ Derivative of Formula I (A=Br, n=1, m=0, R'=bond to chain) by the action of a C$_2$ enol ether on β-ionol 1) preparation of Brominated C$_{15}$ Aldehyde The following reaction was used where Z=Et or SiMe$_3$:

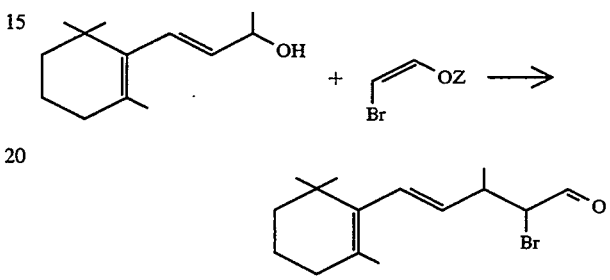

190 μl (or 0.4 equiv.) of boron trifluoride etherate were rapidly added to a solution of 580 mg (3 mmol) of β-ionol and 3 mmol of enol ether in 6 ml of nitroethane, cooled to −20° C., and the mixture was kept stirring at this temperature 1 h 30 min. It was hydrolysed with 5 ml of a saturated aqueous solution of sodium bicarbonate. The mixture was extracted 2 times with 5 ml of pentane and the pentane phase was washed 2 times with 1.5 ml of water, then dried over MgSo$_4$, filtered and concentrated. The expected product was purified by flash chromatography on silica (eluent: pet. eth./Et$_2$O=96/4).

The yield was quantitative in the case of the trimethylsilylated enol ether and it was 64% in the case of the ethyl enol ether.

2) Preparation of the C$_{15}$ Aldehyde (β-ionylideneacetaldehyde)

The following reaction was used:

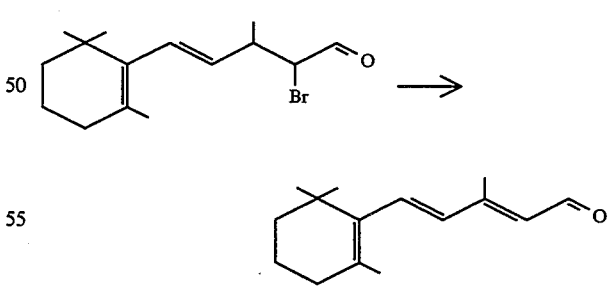

0.9 g (3 mmol) of brominated aldehyde were placed in 8 ml of dichloromethane and then 0.46 ml (1 equiv.) of DBU was added. The mixture was kept stirring for 1 hour and then concentrated and taken up in 5 ml of ether, washed 2 times with 3 ml of water, dried over magnesium sulphate, filtered and concentrated. The crude product was chromatographed on silica (eluent: pet. eth./Et$_2$O=98/2) and 0.43 g of the C$_5$ aldehyde was recovered. The yield was 66%.

EXAMPLE 18

Production of a C$_{15}$ Compound of Formula II A=Cl) by the action of a C$_5$ enol chloroether on a C$_{10}$ alcohol
The following reaction was used:

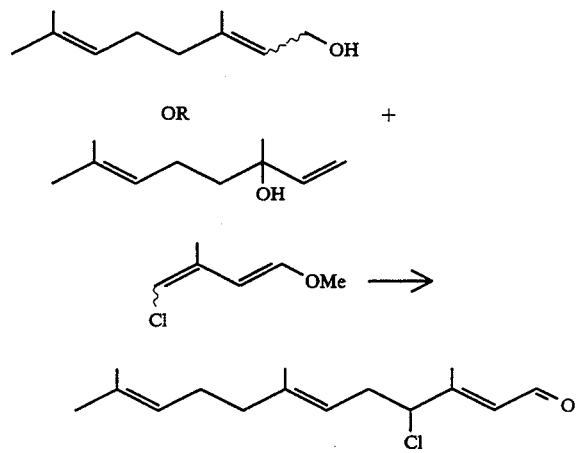

400 mg (3 mmol) of C$_5$ enol chloroether and 1 equiv. of isopropanol were introduced into 4.5 ml of nitroethane. The mixture is cooled to −35° C. and 0.5 equiv. of zinc chloride and 460 mg (3 mmol) of linalol (or a mixture of geraniol and nerol) were added.

After 10 min at −35° C., the mixture was hydrolysed with 6 ml of an aqueous solution of sodium bicarbonate and extracted with dichloromethane.

The expected product was characterized by $^1$H NMR. $^1$H NMR (CDCL$_3$): 10.5 (d, 1H,J=8 Hz).

EXAMPLE 19

Process for Preparing a ψ-dihydroretinal by the Action of an Enol Ether on Vinyl ψ-ionol
The following reaction was used:

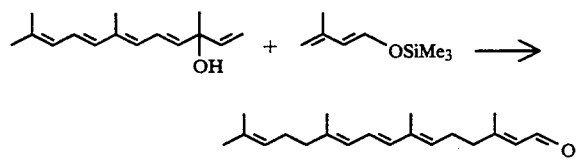

5 ml of formic acid and 1 ml of water were added to a mixture of 660 mg (3 mmol) of vinyl ψ-ionol and 470 mg (3 mmol) of enol ether. The mixture was allowed to react for 30 min at 20° C. and then 3 ml of pentane were added. The pentane phase was washed 2 times with 1.5 ml of water and dried over MgSO$_4$ and then filtered and concentrated. The expected product was purified by flash chromatography on silica (eluent: pet. eth./Et$_2$O=96/4). The yield was 72%.

EXAMPLE 20

Production of a C$_{20}$ Derivative of Formula II (A=Cl) by the action of an enol ether on vinyl ψ-ionol
Preparation of chlorinated C$_{20}$ Aldehyde
The following reaction was used:

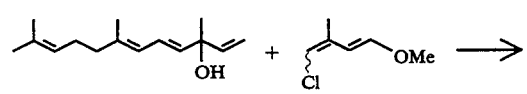

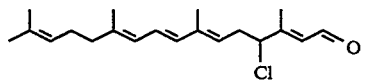

5 ml of formic acid and 1 ml of water were added to a mixture of 600 mg (3 mmol) of vinyl ψ-ionol and 400 mg (3 mmol) of enol ether. The mixture was allowed to react for 30 min at 20° C. and then 3 ml of pentane were added and the pentane phase was washed 2 times with 1.5 ml of water. It was dried over MgSO$_4$ and then filtered and concentrated: the expected product was purified by flash chromatography on silica (eluent: pet. eth./Et$_2$O=06/4). The yield was 63%.

2) Preparation of the Unsaturated C$_{20}$ Aldehyde
The following reaction was used:

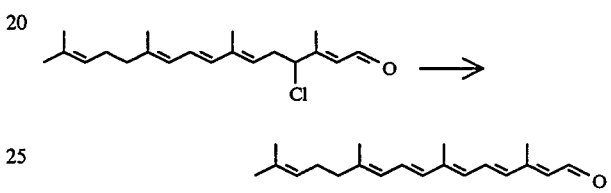

0.23 g (0.71 mmol) of chlorinated C$_{20}$ aldehyde was placed in 2 ml of dichloromethane and then 0.11 ml (1 equiv.) of DBU was added. The mixture was kept stirring for 2 hours and then concentrated and taken up in 5 ml of ether, washed 2 times with 3 ml of water, dried over magnesium sulphate, filtered and concentrated to give 130 mg of unsaturated C$_{20}$ aldehyde. The yield was 64%.

EXAMPLE 21

Production of C$_{18}$ Derivative of Formula II (A=Cl) by the action of a C$_3$ enol ether on vinyl ψ-ional
1) Preparation of chlorinated C$_{18}$ Ketone
The following reaction was used:

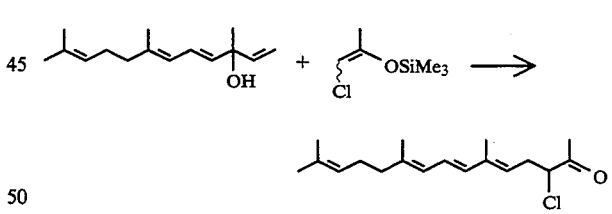

5 ml of formic acid and 1 ml of water were added to a mixture of 660 mg (3 mmol) of vinyl ψ-ionol and 500 mg (3 mol) of enol ether. The mixture was allowed to react for 30 min at 20° C. and then 3 ml of pentane were added and the pentane phase was washed 2 times with 1.5 ml of water. It was dried over MgSO$_4$ and then filtered and concentrated. The expected product was purified by flash chromatography on silica (eluent: pet. eth./Et$_2$O=96.4).

Preparation of the C$_{18}$ Ketone
The following reaction was used:

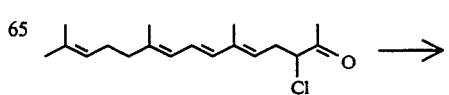

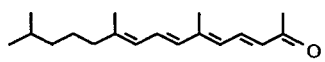

0.41 g (1.4 mmol) of the chlorinated $C_{18}$ ketone was placed in 3 ml of dichloromethane and then 0.21 ml (1 equiv.) of DBU was added. The mixture was kept stirring for 15 hours and then concentrated and taken up in 5 ml of ether, washed 2 times with 3 ml of water, dried over magnesium sulphate, filtered and concentrated to give, after purification by flash chromatography on silica (pet. eth./eth.=96/4), 330 mg of ψ-phytone.

The yield of $C_{18}$ ketone, relative to the vinyl ψ-ionol, was 46%.

EXAMPLE 22

Process for Preparing a $C_{15}$ Derivative by the Action of $C_5$ enol ether on a $c_{10}$ Alcohol The following reaction was used:

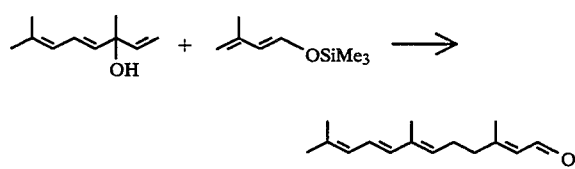

5 ml of formic acid and 1 ml of water were added to a mixture of 456 mg (3 mmol) of the $C_{10}$ alcohol and 460 mg (3 mmol) of the enol ether. The mixture was allowed to react for 30 min at 20° C. and then 3 ml of pentane were added and the pentane phase was washed 2 times with 1.5 ml of water. It was dried over $MgSO_4$ and then filtered and concentrated. The expected product was purified by flash chromatography on silica (eluent: pet. eth./$Et_2O$=96/4). The yield was 65%.

We claim:

1. A process for condensing polyenic compounds, which process comprises reacting a) a compound having the formula III:

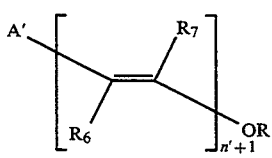

wherein:
n' represents an integer from 0 to 10;
R represents an alkyl group, a silyl group having 1 to 3 substituents selected from methyl, ethyl and phenyl groups, an alkylcarbonyl group or a tosyl group;
$R_6$ and $R_7$ each represent identical or different substituents selected from hydrogen, an alkyl group having one to four carbon atoms, and cyclic alkenyl units and all $R_6$ units need not be identical when n' is an integer from 1 to 10 and all $R_7$ units need not be identical when n' is an integer from 1 to 10;
A' represents a halogen selected from chlorine and bromine, or an arylthio, arylseleno, acyloxy or trialkylsilyl group;
with b) a compound having the formula IV:

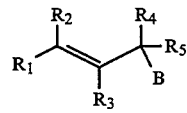

wherein:
$R_1$, $R_2$, $R_3$, $R_4$ and $R_5$ represent hydrogen, an alkyl group having one to twenty carbon atoms, an alkenyl group having two to twenty carbon atoms, or they may form with one another a cyclic, substituted or unsubstituted, terpenic, polyenic alkylene or alkenylene chain;
B represents hydroxyl or an alkoxy group having 1 to 6 carbon atoms, an alkyl carbonyl group, arloxy group, a silyloxy group, or a halogen;
wherein the condensation of the compound of the formula (III) with that of the formula (IV) is carried out in the presence of a Lewis acid or a protic acid and at a temperature ranging from −45° C. to room temperature.

2. A process according to claim 1, wherein the compound of formula (IV) is selected from those having the formulae:

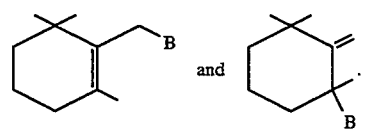

3. A process according to claim 1, wherein the compound of formula (IV) is selected from those having the formulae:

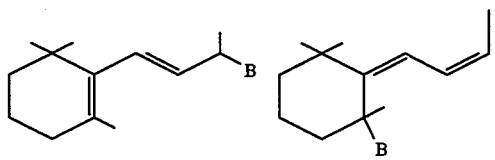

4. A process according to claim 1, wherein the compound of formula (IV) is selected from those having the following formulae:

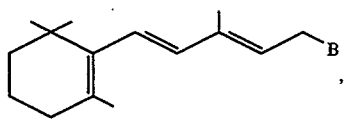

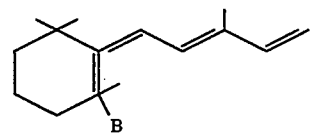

-continued

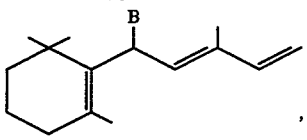

,

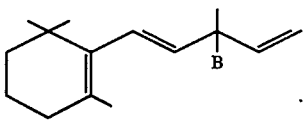

5. A process according to claim 1, wherein the compound of formula (IV) is selected from those having the following formulae:

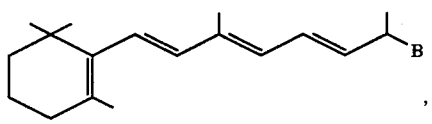

,

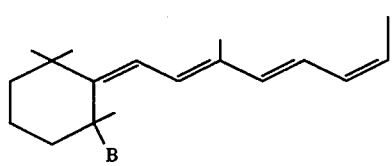

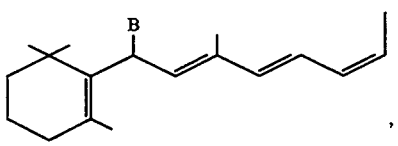

,

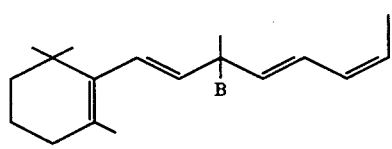

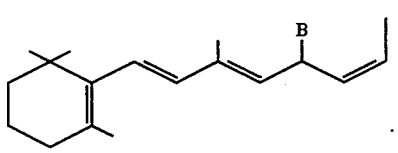

6. A process according to claim 1, wherein the Lewis or protic acid is selected from zinc chloride, boron trifluoride etherate, ferric chloride, trichloroacetic acid, trifluoroacetic acid, trimethylsilyl triflate, stannous or stannic chlorides, formic acid, trifluoromethanesulphonic acid, dimethyl tert-butylsilyl triflate, bismuth trichloride, titanium tetrachloride and heterogeneous acid catalysts.

7. A process according to claim 6, wherein the condensation is further carried out in the presence of at least one solvent selected from an alcohol and water.

8. A process according to claim 6, wherein the condensation is carried out in at least one solvent selected from nitriles, nitroalkanes, nitroaryls, halogenated aliphatic or aromatic solvents, sulphones and organic acids.

9. A process according to claim 8, wherein the temperature of the reaction medium is between about −45° C. and room temperature.

10. A process according to claim 8, wherein the compound of formula IV is selected from those having the formulae:

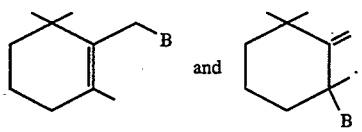 and 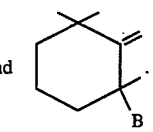

11. A process according to claim 8, wherein the compounds of formula IV is selected from those having the formulae:

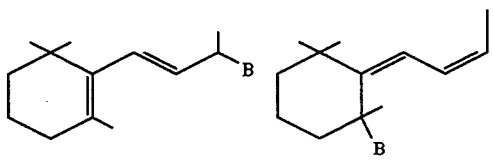 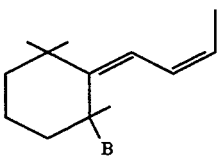

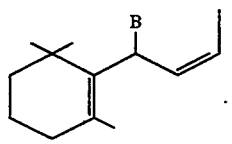

12. A process according to claim 8, wherein the compound of formula IV is selected from those having the formulae:

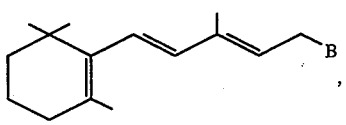

,

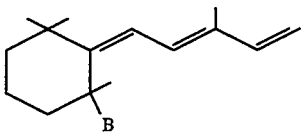

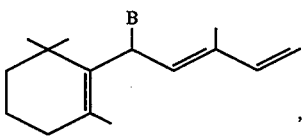

,

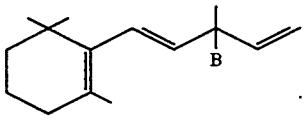

13. A process according to claim 8, wherein the compound of formula IV is selected from those having the formulae:

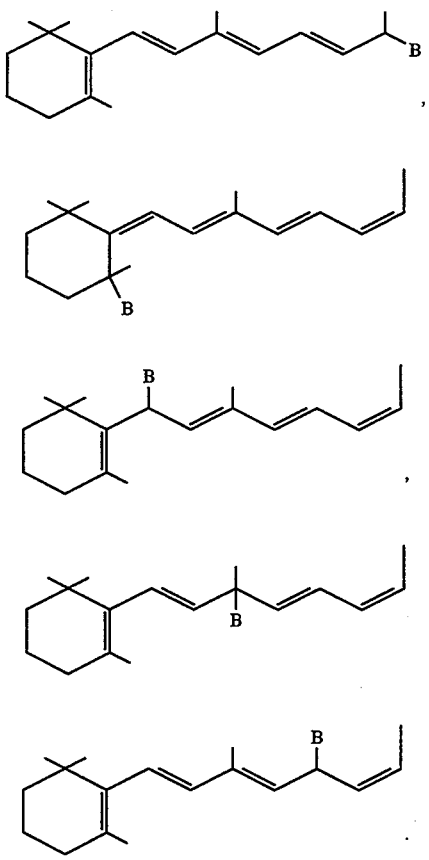

14. A process according to claim 10, wherein the temperature of the reaction medium is from about $-45°$ C. to room temperature.

15. A process according to claim 11, wherein the temperature of the reaction medium is from about $-45°$ C. to room temperature.

16. A process according to claim 12, wherein the temperature of the reaction medium is from about $-45°$ C. to room temperature.

17. A process according to claim 13, wherein the temperature of the reaction medium is from about $-45°$ C. to room temperature.

18. A process according to claim 6 wherein the condensation is carried out in the presence of at least one solvent selected from water and organic acids.

19. A process according to claim 6 wherein the condensation is carried out in the presence of at least one solvent selected from water and formic acid.

20. A process according to claim 19 wherein the temperature of the reaction medium is between about $-45°$ C. and room temperature.

21. A process according to claim 18 wherein the temperature of the reaction medium is between about $-45°$ C. and room temperature.

22. A process for condensing polyenic compounds, which process comprises reacting a) a compound having the formula III:

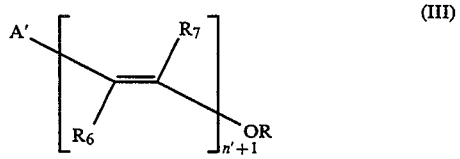

wherein:
n' represents an integer from 0 to 10;
R represents an alkyl group, a silyl group having 1 to 3 substituents selected from methyl, ethyl and phenyl groups, an alkylcarbonyl group or a tosyl group;
$R_6$ and $R_7$ each represent identical or different substituents selected from hydrogen, an alkyl group having one to four carbon atoms, and cyclic alkenyl units and all $R_6$ units need not be identical when n' is an integer from 1 to 10 and all $R_7$ units need not be identical when n' is an integer from 1 to 10;
A' represents hydrogen, a halogen selected from chlorine and bromine, or an arylthio, arylseleno, acyloxy or trialkylsilyl group;
with b) a compound having the formula IV:

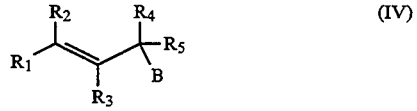

wherein:
$R_1$, $R_2$, $R_3$, $R_4$ and $R_5$ represent hydrogen, an alkyl group having one to twenty carbon atoms, an alkenyl group having two to twenty carbon atoms, or they may form with one another a cyclic, substituted or unsubstituted, terpenic, polyenic alkylene or alkenylene chain;
B represents hydroxyl or an alkoxy group having 1 to 6 carbon atoms, an alkyl carbonyl group, arloxy group, a silyloxy group, or a halogen;
wherein the condensation of the compound of the formula (III) with that of the formula (IV) is carried out in the presence of a Lewis acid or a protic acid and at a temperature ranging from $-45°$ C. to room temperature.

* * * * *